(12) United States Patent
Fujimoto et al.

(10) Patent No.: US 7,711,082 B2
(45) Date of Patent: May 4, 2010

(54) X-RAY CT APPARATUS AND X-RAY CT IMAGING METHOD

(75) Inventors: Ryosuke Fujimoto, Tokyo (JP); Yusuke Nozawa, Tokyo (JP); Akihiko Nishide, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 35 days.

(21) Appl. No.: 12/324,557

(22) Filed: Nov. 26, 2008

(65) Prior Publication Data

US 2009/0180585 A1 Jul. 16, 2009

(30) Foreign Application Priority Data

Nov. 30, 2007 (JP) ............................. 2007-310504

(51) Int. Cl.
*A61B 6/00* (2006.01)
(52) U.S. Cl. ......................................... 378/16; 378/115
(58) Field of Classification Search ............... 378/4–20, 378/98.9, 108, 115
See application file for complete search history.

(56) References Cited

U.S. PATENT DOCUMENTS

| | | | |
|---|---|---|---|
| 4,160,906 A | 7/1979 | Daniels et al. ................. | 378/97 |
| 4,685,118 A | 8/1987 | Furbee et al. ................. | 378/114 |
| 4,813,061 A | 3/1989 | Kakegawa ................. | 378/98.11 |
| 5,200,645 A | 4/1993 | Laeuffer ....................... | 307/82 |
| 6,343,111 B1 | 1/2002 | Avinash et al. ............ | 378/98.11 |
| 7,286,642 B2 | 10/2007 | Ishikawa et al. ............. | 378/111 |
| 7,346,381 B2 | 3/2008 | Okerlund et al. ............. | 600/407 |
| 2003/0142787 A1 | 7/2003 | Jabri et al. ................. | 378/98.12 |
| 2003/0147497 A1 | 8/2003 | Avinash ....................... | 378/98.9 |
| 2008/0095303 A1 | 4/2008 | Grass et al. ..................... | 378/5 |
| 2008/0260092 A1 | 10/2008 | Imai et al. ....................... | 378/5 |

FOREIGN PATENT DOCUMENTS

JP 2007-185371 7/2007

*Primary Examiner*—Courtney Thomas
(74) *Attorney, Agent, or Firm*—Armstrong Teasdale LLP

(57) ABSTRACT

An X-ray CT apparatus includes an X-ray generating section for generating X-rays with a plurality of X-ray tube voltages; a data collecting section for collecting, synchronously with a data collection signal, X-ray projection data from X-rays with each X-ray tube voltage switched by an X-ray tube voltage switching signal; and a control section for controlling a timed moment for switching of the X-ray tube voltage and a timed moment for start of data collection so that the timed moment for start of data collection at each X-ray tube voltage in the data collection signal is delayed relative to the timed moment for switching of the X-ray tube voltage to that X-ray tube voltage in the X-ray tube voltage switching signal by Δt1, Δt2 depending upon imaging conditions.

20 Claims, 9 Drawing Sheets

X-RAY CT APPARATUS AND X-RAY CT IMAGING METHOD

CROSS REFERENCE TO RELATED APPLICATIONS

This application claims the benefit of Japanese Patent Application No. 2007-310504 filed Nov. 30, 2007, which is hereby incorporated by reference in its entirety.

BACKGROUND OF THE INVENTION

The subject matter disclosed herein relates to an X-ray CT (Computed Tomography) apparatus and an X-ray CT imaging method, and particularly to an X-ray CT apparatus or method for conducting imaging using X-rays with a plurality of X-ray tube voltages.

For X-ray CT apparatuses representative of those having a two-dimensional X-ray area detector of a matrix structure, exemplified by a multi-row X-ray detector or flat-panel detector, there have been techniques called dual-energy imaging (or Dual Energy Scan) that produces an image representing a difference of dependency of the X-ray absorption coefficient upon the X-ray tube voltage using tomographic images at a plurality of X-ray tube voltages (e.g., see Japanese Patent Application Laid Open No. 2006-6531).

More specifically stated, in such dual-energy imaging, an X-ray tube generates first X-rays with a first X-ray tube voltage and second X-rays with a second X-ray tube voltage, those voltages being representative of the plurality of X-ray tube voltages, and a data collecting apparatus collects X-ray projection data separately at the plurality of X-ray tube voltages. Based on the X-ray projection data at the first X-ray tube voltage and those at the second X-ray tube voltage, a difference in dependency of the X-ray absorption coefficients upon the X-ray tube voltage between the first and second X-ray tube voltages is represented as an image. By the method, an equivalent image of a certain material can be obtained as an image by dual-energy imaging, in which image a contrast is given between a plurality of different materials that would otherwise be indiscernible in the resulting image because of close CT values if imaging was conducted with a constant X-ray tube voltage.

BRIEF DESCRIPTION OF THE INVENTION

The contrast in the image obtained by dual-energy imaging is larger when a difference between the X-ray projection data value at the first X-ray tube voltage (data value obtained by data collection integration in the data collecting apparatus under the first X-ray tube voltage) and that at the second X-ray tube voltage (data value obtained by data collection integration in the data collecting apparatus under the second X-ray tube voltage) is larger.

Switching between the first and second X-ray tube voltages is made for every view or every several views in response to an X-ray tube voltage switching signal. Moreover, the data collecting section for collecting the X-ray projection data is supplied with a data collection signal to proceed to collection of the X-ray projection data. The data collection signal is synchronous with the X-ray tube voltage switching signal, and as soon as a timed moment for switching of the X-ray tube voltage in the X-ray tube voltage switching signal is reached, collection of X-ray projection data is started.

There exists, however, a time lag from the timed moment for switching of the X-ray tube voltage in the X-ray tube voltage switching signal to the time at which a power of the X-ray detector corresponding to the X-ray tube voltage is attained after switching, which time lag is caused by a time lag due to electric capacity of a high-voltage cable, etc. running from a high-voltage generator to an X-ray tube in the X-ray generating section, a response delay in outputting X-rays after the X-ray tube voltage in the X-ray tube is changed, and a time lag in a response property of the X-ray detector. Therefore, the configuration in which collection of X-ray projection data is started as soon as a timed moment for switching of the X-ray tube voltage in the X-ray tube voltage switching signal is reached, as described above, reduces a difference between the X-ray projection data value at the first X-ray tube voltage and that at the second X-ray tube voltage, resulting in an obscure contrast between different materials in resulting tomographic images by dual-energy imaging with the respective X-ray tube voltages.

In one aspect, an X-ray CT apparatus with optimized control for X-ray data collection to achieve a larger contrast in a resulting image.

In a first aspect an X-ray CT apparatus is provided, comprising: an X-ray generating section for generating X-rays with a plurality of X-ray tube voltages; a data collecting section for collecting, synchronously with a data collection signal, X-ray projection data from X-rays with each X-ray tube voltage switched by an X-ray tube voltage switching signal; and a control section for controlling a timed moment for switching of the X-ray tube voltage and a timed moment for start of data collection so that the timed moment for start of data collection at each X-ray tube voltage in the data collection signal is delayed relative to the timed moment for switching of the X-ray tube voltage to that X-ray tube voltage in the X-ray tube voltage switching signal by a certain period of time depending upon imaging conditions.

In a second aspect according to the first aspect, the delay by a certain period of time is controlled based on the X-ray projection data at each X-ray tube voltage.

In a third aspect according to the first or second aspect, the control section generates the X-ray tube voltage switching signal with reference to the data collection signal so that the timed moment for start of data collection at each X-ray tube voltage in the data collection signal is delayed relative to the timed moment for switching of the X-ray tube voltage to that X-ray tube voltage in the X-ray tube voltage switching signal.

In a fourth aspect according to the first or second aspect, the control section generates the data collection signal with reference to the X-ray tube voltage switching signal so that the timed moment for start of data collection at each X-ray tube voltage in the data collection signal is delayed relative to the timed moment for switching of the X-ray tube voltage to that X-ray tube voltage in the X-ray tube voltage switching signal.

In a fifth aspect according to any one of the first through fourth aspects, the delay by a certain period of time is the same for all operations of switching to another X-ray tube voltage.

In a sixth aspect according to any one of the first through fourth aspects, the delay by a certain period of time is different between operations of switching to another X-ray tube voltage.

In a seventh aspect according to any one of the first through sixth aspects, the X-ray CT apparatus also includes a setting means for setting a period of time from the timed moment for switching of the X-ray tube voltage to each X-ray tube voltage to the timed moment for start of data collection at that X-ray tube voltage.

In an eighth aspect according to the seventh aspect, the period of time from the timed moment for switching of the X-ray tube voltage to each X-ray tube voltage to the timed moment for start of data collection at that X-ray tube voltage is set by said setting means so that an enhanced tomographic image image-reconstructed based on the X-ray projection data at respective X-ray tube voltages has a relatively large contrast between different materials.

In a ninth aspect according to the seventh aspect, the period of time from the timed moment for switching of the X-ray tube voltage to each X-ray tube voltage to the timed moment for start of data collection at that X-ray tube voltage is set by said setting means so that tomographic images at respective X-ray tube voltages image-reconstructed from X-ray projection data at said respective X-ray tube voltages have a relatively large ratio of pixel values representing a specific material.

In a tenth aspect according to any one of the first through ninth aspects, the timed moment for start of data collection at each X-ray tube voltage is a timed moment for start of data collection integration by said data collecting section.

In an eleventh aspect according to any one of the first through tenth aspects, the X-ray CT apparatus also includes a pulse signal generating section for detecting a rotation angle of said X-ray generating section, wherein the period of time from the timed moment for switching of the X-ray tube voltage to each X-ray tube voltage to the timed moment for start of data collection at that X-ray tube voltage is equivalent to or a multiple of the pulse width of the pulse signal generated at said pulse signal generating section.

In a twelfth aspect according to any one of the first through tenth aspects, the X-ray CT apparatus also includes a clock pulse generating section, wherein the period of time from the timed moment for switching of the X-ray tube voltage to each X-ray tube voltage to the timed moment for start of data collection at that X-ray tube voltage is equivalent to or a multiple of the pulse width of the clock pulse signal generated at said clock pulse generating section.

In a thirteenth aspect according to any one of the first through twelfth aspects, the control section makes control to provide a different data collection time for each X-ray tube voltage so that X-ray projection data at respective X-ray tube voltages or tomographic images at respective X-ray tube voltages image-reconstructed based on the X-ray projection data at the respective X-ray tube voltages have equivalent noise.

In a fourteenth aspect according to the thirteenth aspect, the control section makes control to provide a period of time from a timed moment for switching of the X-ray tube voltage to a next timed moment that is different between respective X-ray tube voltages so that X-ray projection data at respective X-ray tube voltages or tomographic images at respective X-ray tube voltages image-reconstructed based on the X-ray projection data at the respective X-ray tube voltages have equivalent noise.

According to the first aspect, since the aforementioned control section controls a timed moment for switching of the X-ray tube voltage and a timed moment for start of data collection so that the timed moment for start of data collection at each X-ray tube voltage is delayed relative to the timed moment for switching of the X-ray tube voltage by a certain period of time depending upon imaging conditions, a difference in X-ray projection data between respective X-ray tube voltages can be optimally widened. Thus, in an image image-reconstructed based on the X-ray projection data at respective X-ray tube voltages, a contrast between different materials can be widened.

According to the second aspect, the aforementioned delay by a certain period of time is controlled based on the X-ray projection data at each X-ray tube voltage, and the timed moment for start of data collection at each X-ray tube voltage is delayed relative to the timed moment for switching of the X-ray tube voltage to that X-ray tube voltage so that a difference in X-ray projection data between respective X-ray tube voltages becomes as large as possible, whereby a contrast between different materials can be further widened in an tomographic image image-reconstructed based on the X-ray projection data at respective X-ray tube voltages.

According to the third aspect, the X-ray tube voltage switching signal is generated with reference to the data collection signal so that the timed moment for start of data collection at each X-ray tube voltage in the data collection signal is delayed relative to the timed moment for switching of the X-ray tube voltage to that X-ray tube voltage in the X-ray tube voltage switching signal, whereby data collection at each X-ray tube voltage can be conducted with a delay from each operation of switching to another X-ray tube voltage.

According to the fourth aspect, the data collection signal is generated with reference to the X-ray tube voltage switching signal so that the timed moment for start of data collection at each X-ray tube voltage in the data collection signal is delayed relative to the timed moment for switching of the X-ray tube voltage to that X-ray tube voltage in the X-ray tube voltage switching signal, whereby data collection at each X-ray tube voltage can be conducted with a delay from each operation of switching to another X-ray tube voltage.

According to the fifth aspect, when the response property of the timed moment for start of data collection at each X-ray tube voltage is the same for each operation of switching to another X-ray tube voltage, a difference in X-ray projection data between respective X-ray tube voltages can be made as large as possible.

According to the sixth aspect, when the response property of the timed moment for start of data collection at each X-ray tube voltage is different between operations of switching to another X-ray tube voltage, a difference in X-ray projection data between respective X-ray tube voltages can be made as large as possible.

According to the seventh aspect, a period of time from the timed moment for switching of the X-ray tube voltage to each X-ray tube voltage to the timed moment for start of data collection at that X-ray tube voltage can be set by the aforementioned setting means to an optimal value such that a difference in X-ray projection data between respective X-ray tube voltages is made as large as possible.

According to the eighth aspect, a period of time from the timed moment for switching of the X-ray tube voltage to each X-ray tube voltage to the timed moment for start of data collection at that X-ray tube voltage is set by the aforementioned setting means so that an enhanced tomographic image image-reconstructed based on the X-ray projection data at respective X-ray tube voltages has a relatively large contrast between different materials, whereby a difference in X-ray projection data between respective X-ray tube voltages can be made as large as possible.

According to the ninth aspect, the aforementioned time difference is set so that tomographic images at respective X-ray tube voltages image-reconstructed from X-ray projection data at the respective X-ray tube voltages have a relatively large ratio of pixel values representing a specific material, whereby a difference in X-ray projection data between respective X-ray tube voltages can be made as large as possible.

According to the tenth aspect, the timed moment for start of data collection integration by the data collecting section can be delayed relative to the timed moment for switching of the X-ray tube voltage to each X-ray tube voltage by a certain period of time.

According to the eleventh aspect, data collection at each X-ray tube voltage is conducted with the period of time from the timed moment for switching of the X-ray tube voltage to each X-ray tube voltage to the timed moment for start of data collection at that X-ray tube voltage being equivalent to or a multiple of the pulse signals generated at the aforementioned pulse signal generating section, whereby a difference in X-ray projection data between respective X-ray tube voltages can be made as large as possible.

According to the twelfth aspect, data collection at each X-ray tube voltage is conducted with the period of time from the timed moment for switching of the X-ray tube voltage to each X-ray tube voltage to the timed moment for start of data collection at that X-ray tube voltage being equivalent to or a multiple of the pulse width of the clock pulse signals generated at the aforementioned clock pulse generating section, a difference in X-ray projection data between respective X-ray tube voltages can be made as large as possible.

According to the thirteenth aspect, since by adjusting a difference of the number of X-ray photons due to a difference between the X-ray tube voltages and that between the corresponding magnitudes of X-ray tube current using the data collection time, optimization can be made so that the S/N ratios in X-ray projection data at respective X-ray tube voltages or in tomographic images at respective X-ray tube voltages become approximately the same, image quality can be improved.

According to the fourteenth aspect, since by adjusting a difference of the number of X-ray photons due to a difference between the X-ray tube voltages and that between the corresponding magnitudes of X-ray tube current using, in addition to the data collection time, the X-ray emission time under each X-ray tube voltage, optimization can be made so that the S/N ratios in X-ray projection data at respective X-ray tube voltages or in tomographic images at respective X-ray tube voltages become approximately the same, image quality can be improved.

DETAILED DESCRIPTION OF THE INVENTION

Several embodiments of the present invention will now be described in detail based on the accompanying drawings.

Figure 1:
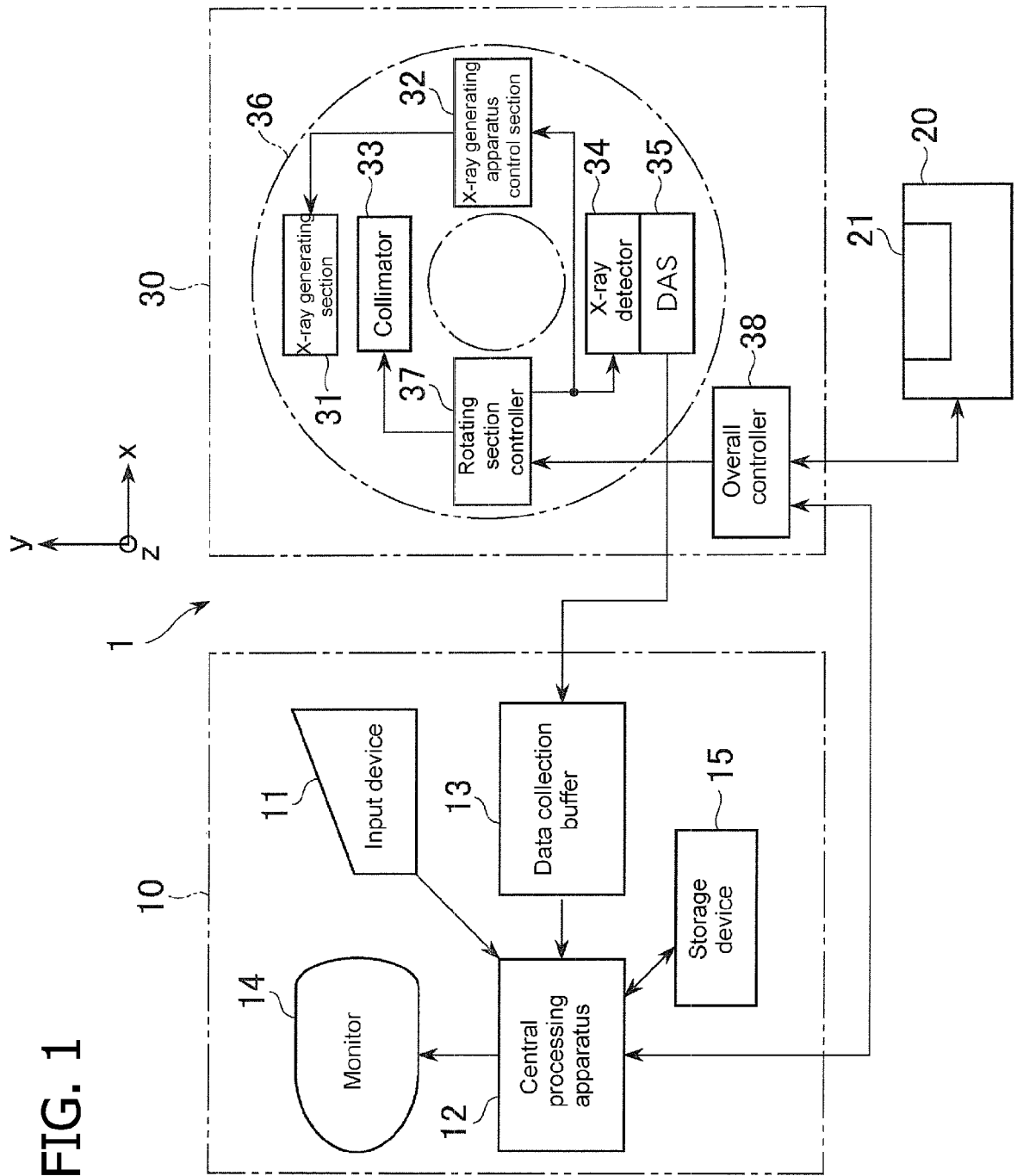
FIG. 1 is a block diagram schematically showing a configuration of an X-ray CT apparatus in accordance with a first embodiment of the present invention.

To begin with, a first embodiment of the present invention will be described. FIG. 1 is a block diagram schematically showing a configuration of an X-ray CT apparatus in accordance with a first embodiment of the present invention.

The X-ray CT apparatus 1 shown in FIG. 1 comprises an operator console 10, an imaging table 20, and a scan gantry 30.

The operator console 10 comprises an input device 11 for accepting an input by a human operator, a central processing apparatus 12 for performing pre-processing, image reconstruction processing, post-processing, and the like, and a data collection buffer 13 for collecting X-ray detector data collected at the scan gantry 30. Moreover, the operator console 10 further comprises a monitor 14 for displaying a tomographic image image-reconstructed from projection data obtained by pre-processing the X-ray detector data, and a storage device 15 for storing programs, X-ray projection data, X-ray tomographic images, and the like.

Figure 2:
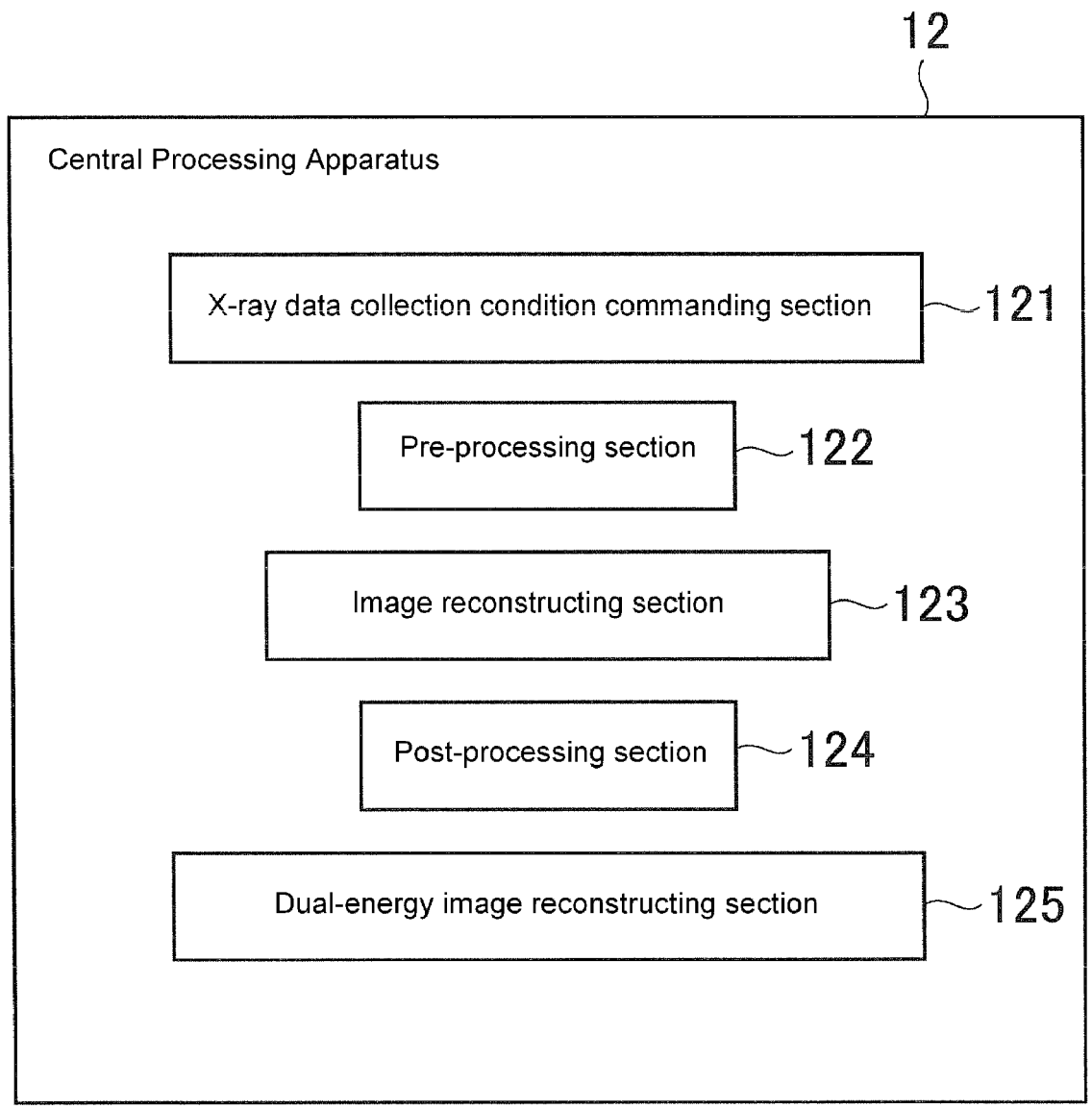
FIG. 2 is a block diagram schematically showing a configuration of a central processing apparatus in the X-ray CT apparatus shown in FIG. 1.

As shown in FIG. 2, the central processing apparatus 12 has an X-ray data collection condition commanding section 121, a pre-processing section 122, an image reconstructing section 123, a post-processing section 124, and a dual-energy image reconstructing section 125.

The X-ray data collection condition commanding section 121 is configured to output an X-ray emission time (a period of time from a timed moment for switching of the X-ray tube voltage to a next timed moment in an X-ray tube voltage switching signal) for emission from an X-ray generating section 31 (which will be described later), a data collection integration time (a data collection integration time in a data collection signal) by the data collecting apparatus 35 (which will be described later), and the like, to an overall controller 38 (which will be described later) as command signals. In this embodiment, the X-ray generating section 31 is configured to generate therefrom a plurality of different X-ray tube voltages, and the X-ray data collection condition commanding section 121 is configured to output a period of time (TW1, TW2, which will be described later) from a timed moment for start of data collection at each X-ray tube voltage to a timed moment for switching of the X-ray tube voltage to each X-ray tube voltage, or a period of time from the timed moment for switching of the X-ray tube voltage to each X-ray tube voltage to the timed moment for start of data collection at each X-ray tube voltage ($\Delta t1$, $\Delta t2$, which will be described later), all of which are stored in the storage device 15 in the operator console 10, to the overall controller 38 as command signals.

The pre-processing section 122 applies offset correction and logarithmic conversion, and further, X-ray dose correction and channel-to-channel correction to the X-ray projection data collected at the data collecting apparatus 35. The image reconstructing section 123 applies beam hardening correction, z-filter convolution processing, reconstruction function convolution processing, and three-dimensional back-projection processing to the pre-processed X-ray projection data. The post-processing section 124 is configured to apply post-processing including image filter convolution, CT value conversion, etc., to the back-projected data. A tomographic image can thus be obtained.

The imaging table 20 has a cradle 21 with a subject laid thereon for insertion into and withdrawal out of an opening of the scan gantry 30. The cradle 21 is configured to vertically moved or horizontally translated along the table by a motor (not shown) embedded in the imaging table 20.

The scan gantry 30 comprises an X-ray generating section 31 comprised of an X-ray tube and a high-voltage generator, an X-ray generating apparatus control section 32, a collimator 33, a multi-row X-ray detector 34, a data collecting apparatus (DAS: Data Acquisition System) 35, and a rotating section 36 that revolves around a body axis of a subject by a motor (not shown). The motor is provided with an encoder (not shown) for detecting a rotation angle of the X-ray generating section 31. The encoder represents the pulse signal generating section as recited in claim 11.

Moreover, the scan gantry 30 comprises a rotating section controller 37 for controlling the rotating section 36, and an overall controller 38 for making communication with the rotating section controller 37 and exchanging control signals or the like with the operator console 10 and imaging table 20.

The X-ray generating section 31 is configured to generate, as X-rays a with plurality of different X-ray tube voltages, first X-rays with a first X-ray tube voltage and second X-rays with a second X-ray tube voltage. In this embodiment, the first X-ray tube voltage is assumed to be higher than the second X-ray tube voltage. For example, the first X-ray tube voltage is 140 kV, and the second X-ray tube voltage is 80 kV.

In this embodiment, based on the X-ray projection data obtained by data collection started after switching to the first X-ray tube voltage, i.e., X-ray projection data collected under the first X-ray tube voltage, and X-ray projection data obtained by data collection started after switching to the second X-ray tube voltage, i.e., X-ray projection data collected under the second X-ray tube voltage, the dual-energy image reconstructing section 125 performs image reconstruction for a tomographic image by dual-energy imaging.

Now switching between the first and second X-ray tube voltages will be described. Switching of the X-ray tube voltage is made for every view or every several views. The X-ray tube voltage switching signal for switching between the first and second X-ray tube voltages is output from the rotating section controller 37. Specifically, an X-ray tube voltage switching signal output from the rotating section controller 37 is input to the X-ray generating apparatus control section 32, which causes the X-ray tube voltage at the X-ray generating section 31 to be switched.

The X-ray tube voltage switching signal is square wave (see FIG. 3), which causes the X-ray generating section 31 to emit first X-rays with the first X-ray tube voltage when at High level, while it causes the X-ray generating section 31 to emit second X-rays with the second X-ray tube voltage when at Low level, for example; by such a signal, tube voltage switching control by the X-ray generating apparatus control section 32 is achieved. That is, a time at which the tube voltage switching signal transitions from Low level to High level, and that at which it transitions from High level to Low level represent the timed moment for switching of the X-ray tube voltage. Alternatively, a different timed moment for switching of the X-ray tube voltage may be applied.

The rotating section controller 37 is configured to generate the X-ray tube voltage switching signal such that the timed moment for start of data collection at each X-ray tube voltage (the timed moment at which collection of X-ray projection data at each X-ray tube voltage is to be started) in a data collection signal (which will be described later) is delayed relative to the timed moment for switching of the X-ray tube voltage in an X-ray tube voltage switching signal by a certain period of time.

Now the X-ray tube voltage switching signal will be described. The X-ray data collection condition commanding section 121 in the central processing apparatus 12 is configured to output command signals to the rotating section controller 37 via the overall controller 38 to generate an X-ray tube voltage switching signal such that a period of time from the timed moment for switching of the X-ray tube voltage to the first X-ray tube voltage in the X-ray tube voltage switching signal to the timed moment for start of data collection under the first X-ray tube voltage in the data collection signal is $\Delta t1$, and a period of time from the timed moment for switching of the X-ray tube voltage to the second X-ray tube voltage in the X-ray tube voltage switching signal to the timed moment for start of data collection under the second X-ray tube voltage in the data collection signal is $\Delta t2$. The rotating section controller 37 is configured to then generate the data collection signal as well, which will be discussed later, and on receipt of the command signals, the rotating section controller 37 generates an X-ray tube voltage switching signal with reference to the data collection signal. That is, the rotating section controller 37 is for controlling the timed moment for switching of the X-ray tube voltage and timed moment for start of data collection so that the timed moment for start of data collection at each X-ray tube voltage is delayed relative to the timed moment for switching of the X-ray tube voltage to each X-ray tube voltage by a certain period of time $\Delta t1$, $\Delta t2$, wherein the controller represents an exemplary embodiment of the control section in the present invention. Moreover, a period of time from a timed moment for switching of the X-ray tube voltage to a next timed moment for switching, i.e., a period of time in which the signal level of the X-ray tube voltage switching signal remains at High level or Low level is also supplied by the X-ray data collection condition commanding section 121 to the rotating section controller 37 to generate a corresponding X-ray tube voltage switching signal. The method of generating the X-ray tube voltage switching signal will be discussed in more detail later.

The data collecting apparatus 35 is configured to conduct collection of X-ray projection data by applying integration and A/D conversion to detector signals from the multi-row X-ray detector 34 that has received X-rays from the X-ray generating section 31, and output them to the data collection buffer 13. The data collecting apparatus 35 is for collection of X-ray projection data at the first X-ray tube voltage and those at the second X-ray tube voltage; collection of the X-ray projection data at respective X-ray tube voltages is conducted on a view-by-view basis when the X-ray tube voltage is switched on a per-view basis, or alternatively, is conducted for every several views when the X-ray tube voltage is switched for every several views.

Now control of X-ray projection data collection in the data collecting apparatus 35 will be described. In this embodiment, the data collection signal for collecting the X-ray projection data generated according to an encoder pulse signal or clock pulse signal is output from the rotating section controller 37, as will be discussed later. The data collection signal output from the rotating section controller 37 is supplied to the data collecting apparatus 35.

Figure 3:
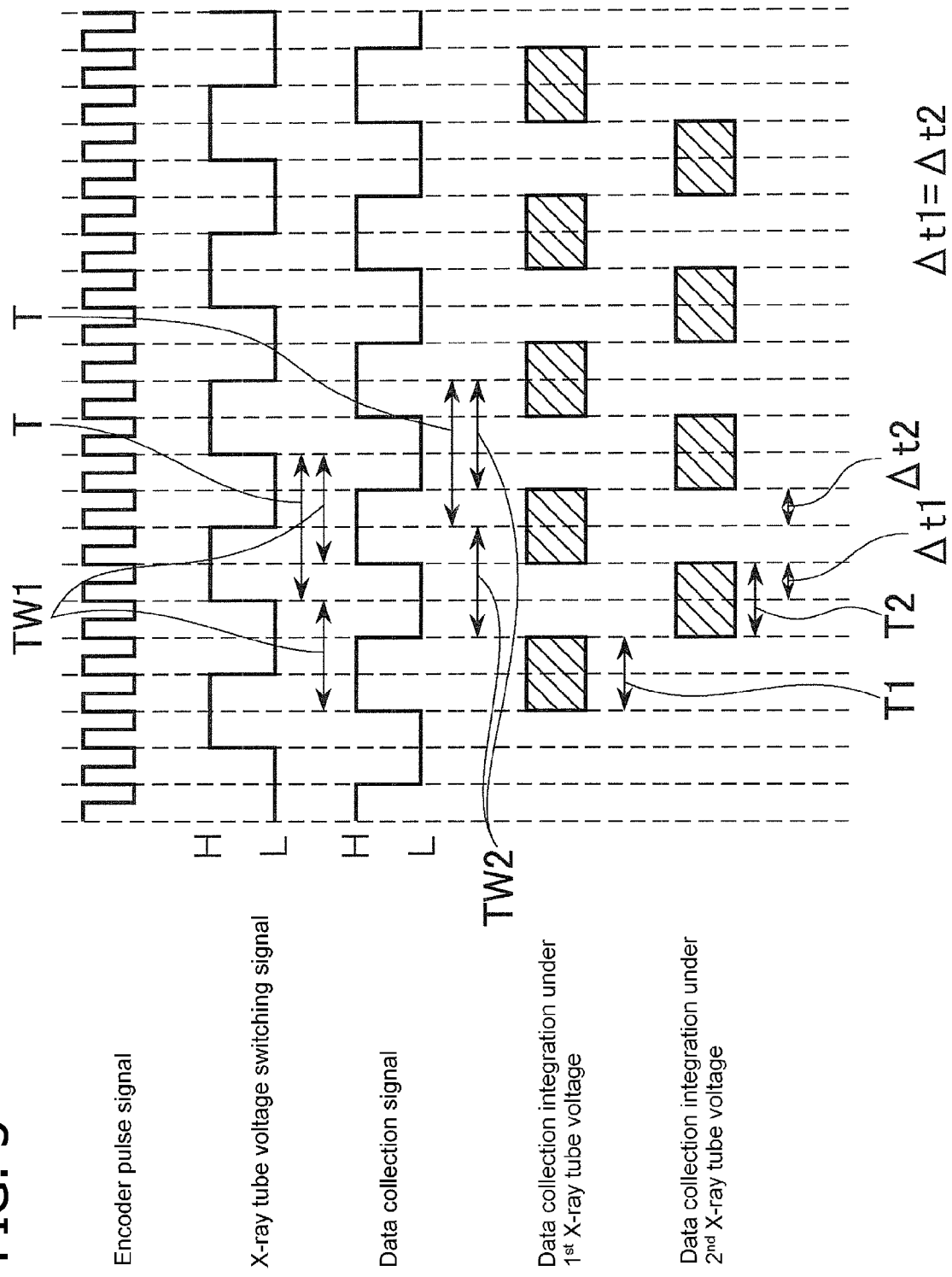
FIG. 3 is a diagram for explaining X-ray projection data collection in the X-ray CT apparatus in the first embodiment.

The data collection signal is square wave (see FIG. 3). Now a timed moment for start of data collection at each X-ray tube voltage in such a data collection signal will be described hereinbelow. The timed moment for start of data collection as used herein refers to a timed moment for start of data collection integration at the data collecting apparatus 35.

After $\Delta t1$ from a timed moment for switching to the first X-ray tube voltage, the data collection signal transitions from Low level to High level, whereupon data collection integration at the first X-ray tube voltage is started at the data collecting apparatus 35. That is, a time at which the data collection signal becomes High level represents the timed moment for start of data collection for the first X-ray tube voltage. The data collection integration continues while the data collection signal remains at High level. Data collection integration started after switching to the first X-ray tube voltage, i.e., data collection integration under the data collection signal at High level, will be sometimes referred to as data collection integration at the first X-ray tube voltage hereinbelow, and the data collected during that time will be sometimes referred to as X-ray projection data at the first X-ray tube voltage.

Moreover, after $\Delta t2$ from the timed moment for switching to the second X-ray tube voltage, the data collection signal transitions from High level to Low level, whereupon data collection integration at the second X-ray tube voltage is started as new data collection integration at the data collecting apparatus 35. That is, a time at which the data collection signal becomes Low level represents the timed moment for start of data collection for the second X-ray tube voltage. The data collection integration continues while the data collection signal remains at Low level. Data collection integration started after switching to the second X-ray tube voltage, i.e., data collection integration under the data collection signal at Low level, will be sometimes referred to as data collection integration at the second X-ray tube voltage hereinbelow, and the data collected during the time will be sometimes referred to as X-ray projection data at the second X-ray tube voltage.

The data collection integration times under the first and second X-ray tube voltages are supplied by the X-ray data collection condition commanding section 121 to the rotating section controller 37 via the overall controller 38. The rotating section controller 37 is configured to then generate a data collection signal to achieve the input data collection integration times, as will be discussed later.

Now an operation of the X-ray CT apparatus 1 will be described. The X-ray CT apparatus 1 conducts collection of X-ray projection data for first and second X-ray tube voltages, by rotating the X-ray generating section 31 and X-ray detector 34 around the subject and translating the cradle 21 to achieve helical scanning. FIG. 3 is a diagram for explaining X-ray projection data collection in the X-ray CT apparatus 1.

In FIG. 3, when the X-ray tube voltage switching signal has become High level, switching to the first X-ray tube voltage is made. On the other hand, when the X-ray tube voltage switching signal has become Low level, switching to the second X-ray tube voltage is made.

When the data collection signal has become High level, data collection integration at the first X-ray tube voltage is started at the data collecting apparatus 35. When the data collection signal has become Low level, new data collection integration, i.e., data collection integration at the second X-ray tube voltage, is started at the data collecting apparatus 35.

Now generation of the X-ray tube voltage switching signal and data collection signal will be described in detail below. The X-ray tube voltage switching signal and data collection signal are generated at the rotating section controller 37. The rotating section controller 37 is supplied with an encoder pulse signal from a motor (not shown) for rotating the rotating section 36, and based on the encoder pulse signal, the rotating section controller 37 first generates a data collection signal. In particular, the rotating section controller 37 divides the frequency of the encoder pulse signal to generate a data collection signal so that a data collection integration time T1 under the first X-ray tube voltage and a data collection integration time T2 under the second X-ray tube voltage are equal to a time supplied by the data collection condition commanding section 121.

It should be noted that the data collection integration time T1 under the first X-ray tube voltage and the data collection integration time T2 under the second X-ray tube voltage are both half the cycle T of the data collection signal and X-ray tube voltage switching signal, i.e., T/2.

The generation of the data collection signal at the rotating section controller 37 is not limited to that based on the encoder pulse. For example, a clock pulse signal may be generated at the rotating section controller 37 or overall controller 38, and the data collection signal may be generated based on the clock pulse signal.

Next, the rotating section controller 37 generates the X-ray tube voltage switching signal with reference to the data collection signal. At that time, the rotating section controller 37 generates the X-ray tube voltage switching signal such that the timed moment for switching of the X-ray tube voltage precedes the timed moment for start of data collection at each X-ray tube voltage by $\Delta t1$ and $\Delta t2$.

Specifically, on receipt of the command signals from the data collection condition commanding section 121, the rotating section controller 37 generates an X-ray tube voltage switching signal such that the signal level transitions from Low level to High level when a period of time from the timed moment for start of data collection integration at the first X-ray tube voltage in the data collection signal (the time at which the signal transitions from Low level to High level) has reached TW1, and the signal level has transitions from High level to Low level when a period of time from the timed moment for start of data collection integration at the second X-ray tube voltage in the data collection signal (the time at which the signal transitions from High level to Low level) has reached TW2. The command signals from the data collection signal commanding section 121 are represented by TW1 and TW2 here.

Now TW1, TW2 will be described. The cycles of the data collection signal and X-ray tube voltage switching signal are both T, and TW1 is defined so that T−TW1 is equal to $\Delta t1$. Likewise, TW2 is defined so that T−TW2 is equal to $\Delta t2$. Therefore, by generating the X-ray tube voltage switching signal as described above, a period of time from the timed moment for switching to the first X-ray tube voltage to the timed moment for start of data collection integration at the first X-ray tube voltage is $\Delta t1$, and a period of time from the timed moment for switching to the second X-ray tube voltage to the timed moment for start of data collection integration at the second X-ray tube voltage is $\Delta t2$.

It should be noted that a period of time in which the X-ray tube voltage switching signal remains at High level (a period of time from the timed moment for switching of the X-ray tube voltage to the first X-ray tube voltage to the timed moment for switching of the X-ray tube voltage to the second X-ray tube voltage, which is the next timed moment for switching of the X-ray tube voltage) is equal to a period of time in which the signal remains at Low level (a period of time from the timed moment for switching of the X-ray tube voltage to the second X-ray tube voltage to the timed moment for switching of the X-ray tube voltage to the first X-ray tube voltage, which is the next timed moment for switching of the X-ray tube voltage) in this embodiment.

$\Delta t1$ and $\Delta t2$ have values such that, when the X-ray absorption coefficient of a certain material under the first X-ray tube voltage is different from that under the second X-ray tube voltage, a difference in X-ray projection data between respective X-ray tube voltages, i.e., a difference between a value of X-ray projection data for a specific material collected under the first X-ray tube voltage (a data value obtained by the data collecting apparatus 35, which will be described below, performing data collection integration at the first X-ray tube voltage) and a value of X-ray projection data for the specific material collected under the second X-ray tube voltage (a data value obtained by the data collecting apparatus 35, which will be described below, performing data collection integration at the second X-ray tube voltage) becomes as large as possible. $\Delta t1$ and $\Delta t2$ that cause the difference between the value of X-ray projection data at the first X-ray tube voltage and that at the second X-ray tube voltage to be as large as possible vary according to imaging conditions (e.g., delay in generation of the X-ray tube voltage or current, capacity of the X-ray tube, capacity of the high-voltage generator (not shown), capacity of a cable (not shown) connecting the high-voltage generator and X-ray tube, delay in the response property of the X-ray detector 34, etc.). Therefore, when the X-ray absorption coefficient of a certain material under the first X-ray tube voltage is different from that under the second X-ray tube voltage, $\Delta t1$ and $\Delta t2$ have values set according to imaging conditions so that a difference between the value of X-ray projection data at the first X-ray tube voltage and that at the second X-ray tube voltage is as large as possible.

Now a method of setting $\Delta t1$ and $\Delta t2$ will be described. $\Delta t1$ and $\Delta t2$ are set so that a contrast in a tomographic image by dual-energy imaging is relatively large (preferably, the largest), taking account of the response property of the X-ray generating section 31 consisting of the X-ray tube, high-voltage generator, and cable, and the response property of the X-ray detector. Alternatively, $\Delta t1$ and $\Delta t2$ may be set so that a ratio of pixel values of a specific material in tomographic images at respective X-ray tube voltages image-reconstructed from the X-ray projection data at respective X-ray tube voltages is relatively large (preferably, the largest).

In particular, in a case that $\Delta t1$ and $\Delta t2$ are set so that a contrast in a tomographic image by dual-energy imaging is relatively large, for example, collection of X-ray projection data is made with varying values of $\Delta t1$ and $\Delta t2$ according to imaging conditions specified by the operator, and tomographic images by dual-energy imaging are image-reconstructed based on the X-ray projection data for respective values. The operator then compares the resulting images with each other and inputs the values of $\Delta t1$ and $\Delta t2$ that give a relatively large contrast, via the input device 11 for an image.

Alternatively, in a case that $\Delta t1$ and $\Delta t2$ are set so that a ratio of pixel values of a specific material in tomographic images image-reconstructed from X-ray projection data at respective X-ray tube voltages is relatively large, for example, collection of X-ray projection data is made with varying values of $\Delta t1$ and $\Delta t2$ according to imaging conditions specified by the operator, similarly to above, and for these values, a tomographic image is image-reconstructed based on the X-ray projection data at the first X-ray tube voltage and a tomographic image is image-reconstructed based on the X-ray projection data at the second X-ray tube voltage. The operator then compares the resulting tomographic images with each other and inputs $\Delta t1$ and $\Delta t2$ that give a relatively large ratio between the pixel value of the specific material in a tomographic image at the first X-ray tube voltage and that at the second X-ray tube voltage, via the input device 11.

The values of $\Delta t1$ and $\Delta t2$ input via the input device 11 as described above are stored in the storage device 15 by the central processing apparatus 12. Setting of $\Delta t1$ and $\Delta t2$ is thus completed (wherein the input device 11 and central processing apparatus represent the setting means as recited in claims 7, 8 and 9). Based on set $\Delta t1$ and $\Delta t2$, TW1 and TW2 are then calculated for storage in the storage device 15.

It should be noted that $\Delta t1$ and $\Delta t2$ set once may be modified when, for example, a material to be observed is changed. In this case, setting is also made by the method as described above.

Figure 4:
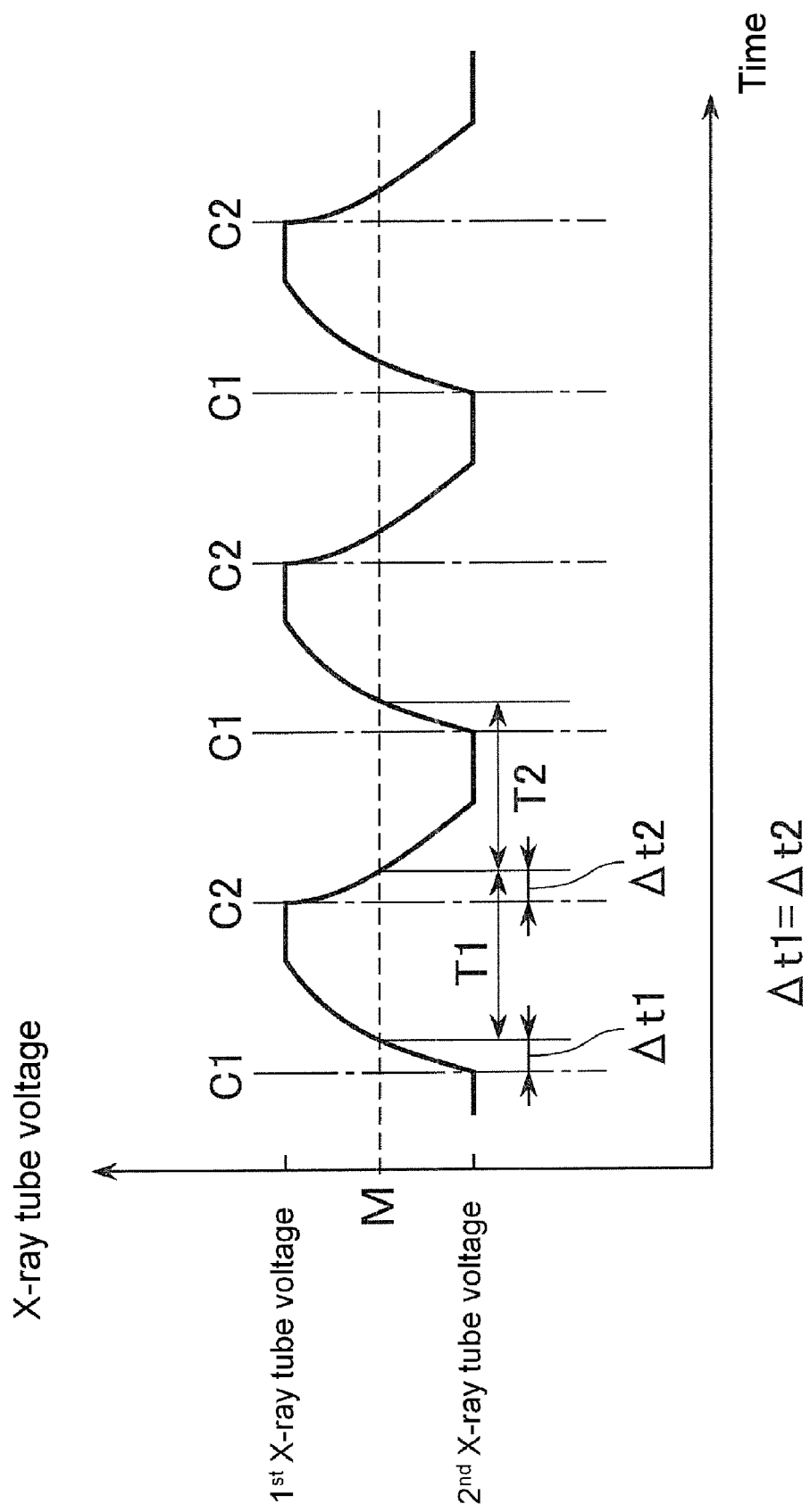
FIG. 4 is a schematic diagram showing an example of the X-ray tube voltage property.

In this embodiment, $\Delta t1$ and $\Delta t2$ have a time width twice the pulse width of the encoder pulse signal (or clock pulse signal) and $\Delta t1=\Delta t2$, which is the same in all operations of switching to another the X-ray tube voltage. By thus defining $\Delta t1=\Delta t2$, a difference in values of X-ray projection data between respective X-ray tube voltages can be made as large as possible when the X-ray tube voltage property is the same in each operation of switching to another X-ray tube voltage. More specifically, FIG. 4 is a schematic diagram showing an example of the X-ray tube voltage property, wherein data collection integration at the first X-ray tube voltage is made when the X-ray tube voltage reaches or exceeds M, which is the midpoint of the first and second X-ray tube voltages, and data collection integration at the second X-ray tube voltage is made when the X-ray tube voltage decreases down to or below M, which is the midpoint of the first and second X-ray tube voltages, for example, whereby a difference in values of X-ray projection data between respective X-ray tube voltages can be made as large as possible. In this case, a period of time from the timed moment C1 for switching of the X-ray tube voltage to the first X-ray tube voltage indicated by a dot-dash line in FIG. 4 to a time at which the midpoint M of the first and second X-ray tube voltages is reached represents $\Delta t1$, and a period of time from the timed moment C2 for switching of the X-ray tube voltage to the second X-ray tube voltage, similarly indicated by a dot-dash line, to a time at which the midpoint M of the first and second X-ray tube voltages is reached represents $\Delta t2$. In the X-ray tube voltage property shown in FIG. 4, the period of time $\Delta t1$ from the timed moment C1 for switching of the X-ray tube voltage to the first X-ray tube voltage to a time at which the tube voltage reaches the midpoint M of the first and second X-ray tube voltages is the same as the period of time $\Delta t2$ from the timed moment C2 for switching of the X-ray tube voltage to the second X-ray tube voltage to a time at which the tube voltage reaches the midpoint M of the first and second X-ray tube voltages, i.e., $\Delta t1=\Delta t2$.

While the preceding description has been made on a case in which the rotating section controller 37 generates the X-ray tube voltage switching signal with reference to the data collection signal, the rotating section controller 37 may first generate the X-ray tube voltage switching signal based on the encoder pulse signal (or clock pulse signal), and thereafter generate the data collection signal with reference to the X-ray tube voltage switching signal. In this case, similarly, the data collection signal is generated so that the timed moment for start of data collection in the data collection signal is delayed relative to the timed moment for switching of the X-ray tube voltage in the X-ray tube voltage switching signal by $\Delta t1$ and $\Delta t2$. In particular, in response to a command signal from the data collection signal, the rotating section controller 37 generates the data collection signal such that the signal level transitions from Low level to High level when a period of time from the timed moment for switching of the X-ray tube voltage to the first X-ray tube voltage in the X-ray tube voltage switching signal (from Low level to High level) reaches $\Delta t1$, and the signal level transitions from High level to Low level when a period of time from the timed moment for switching of the X-ray tube voltage to the second X-ray tube voltage in the X-ray tube voltage switching signal (from High level to Low level) reaches $\Delta t2$. In this case, a command signal from the data collection signal commanding section 121 represents $\Delta t1$ and $\Delta t2$.

Once X-ray projection data at the first X-ray tube voltage has been collected so that a period of time from the timed moment C1 for switching of the X-ray tube voltage to the first X-ray tube voltage to the timed moment for start of data collection integration at the first X-ray tube voltage is $\Delta t1$, and X-ray projection data at the second X-ray tube voltage has been collected so that a period of time from the timed moment C2 for switching of the X-ray tube voltage to the second X-ray tube voltage to the timed moment for start of data collection integration at the second X-ray tube voltage is $\Delta t2$, the image reconstructing section 123 image-reconstructs a tomographic image at the first X-ray tube voltage based on the X-ray projection data at the first X-ray tube voltage, and a tomographic image at the second X-ray tube voltage based on the X-ray projection data at the second X-ray tube voltage. In image-reconstructing the tomographic image at the first X-ray tube voltage, only X-ray projection data at the first X-ray tube voltage are extracted and combined together for every view or every several views, and then, image reconstruction for a tomographic image at the first X-ray tube voltage is performed. Similarly, in image-reconstructing the tomographic image at the second X-ray tube voltage, only X-ray projection data at the second X-ray tube voltage are extracted and combined together for every view or every several views, and then, image reconstruction for a tomographic image at the second X-ray tube voltage is performed.

The dual-energy image reconstructing section 125 then applies weighted addition processing using predetermined weighted addition factors for these tomographic images to image-reconstruct a tomographic image by dual-energy imaging (e.g., calcium-enhanced tomographic image, and contrast-enhanced tomographic image), which is an enhanced tomographic image of different materials, and the resulting image is displayed on the aforementioned monitor 14.

According to the X-ray CT apparatus 1 of the present embodiment, the timed moment for start of data collection at each X-ray tube voltage is delayed relative to the timed moment for each operation of switching to another X-ray tube voltage by $\Delta t1$ and $\Delta t2$, whereby a difference between a value of X-ray projection data at the first X-ray tube voltage and that at the second X-ray tube voltage can be made as large as possible. Thus, a contrast between different materials can be widened in a tomographic image by dual-energy imaging.

Next, a second embodiment will be described. In the following description, only differences thereof from the first embodiment will be explained.

Figure 5:
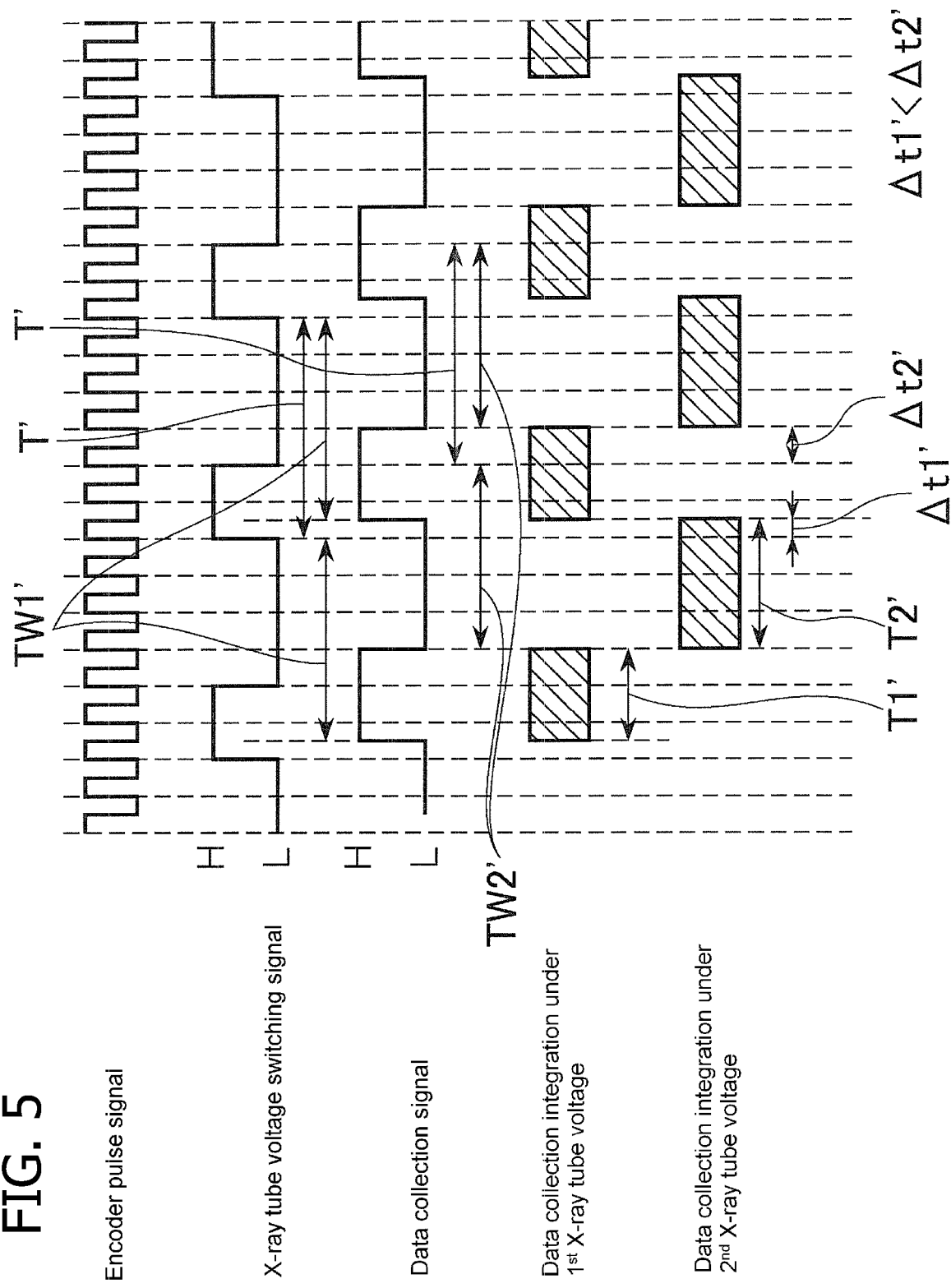
FIG. 5 is a diagram for explaining X-ray projection data collection in the X-ray CT apparatus in a second embodiment.

FIG. 5 is a diagram for explaining X-ray projection data collection in the X-ray CT apparatus in the second embodiment. As shown in FIG. 5, in this embodiment, a period of time $\Delta t1'$ from the timed moment for switching of the X-ray tube voltage to the first X-ray tube voltage to the timed moment for start of data collection integration at the first X-ray tube voltage (i.e., a difference between T' (a cycle of the data collection signal and X-ray tube voltage switching signal) and TW1' (a period of time after the data collection signal has transitioned from Low level to High level until the X-ray tube voltage switching signal transitions from Low level to High level)) has a value different from that of a period of time $\Delta t2'$ from the timed moment for switching to the second X-ray tube voltage to the timed moment for start of data collection integration at the second X-ray tube voltage (i.e., a difference between T' and TW2' (a period of time after the data collection signal has transitioned from High level to Low level until the X-ray tube voltage switching signal transitions from High level to Low level)), resulting in different delay times from the timed moment for switching of the X-ray tube voltage to the timed moment for start of data collection between respective operations of switching to another X-ray tube voltage. By thus defining $\Delta t1'$ and $\Delta t2'$ as different values, a difference in values of X-ray projection data for a certain material between respective X-ray tube voltages can be made as large as possible when the X-ray tube voltage property varies for each operation of switching to another X-ray tube voltage (which will be described later with reference to FIG. 6).

Figure 6:
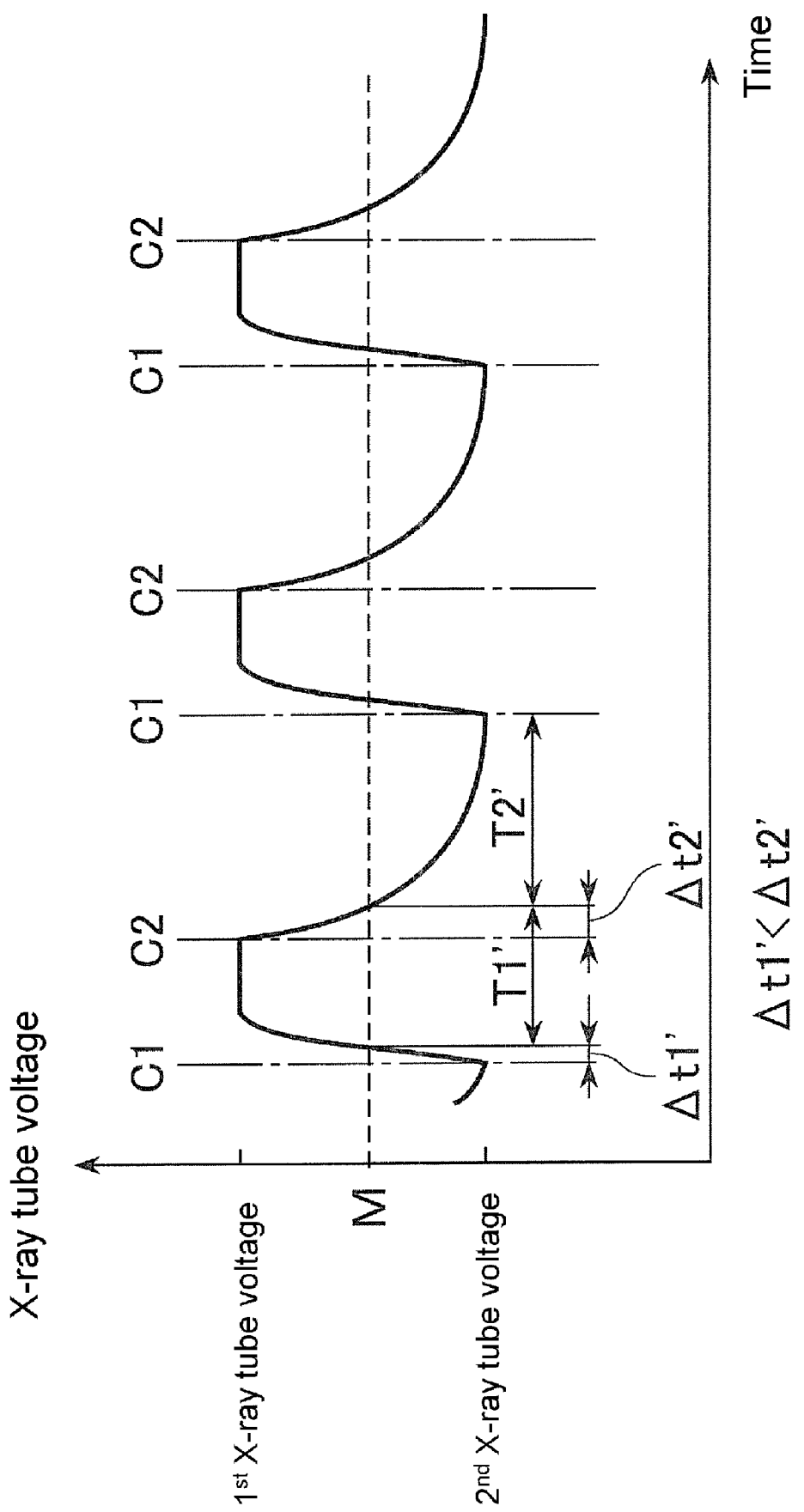
FIG. 6 is a schematic diagram showing an example of the X-ray tube voltage property.

According to the present embodiment, $\Delta t1' < \Delta t2'$, where $\Delta t1'$ represents a time width equal to the pulse width of the encoder pulse signal (or clock pulse signal), and $\Delta t2'$ represents a time width twice the pulse width of the encoder pulse signal (clock pulse signal). Accordingly, TW1', TW2' and T' are defined to achieve such $\Delta t1'$ and $\Delta t2'$. The following description will address the X-ray tube voltage property in a case that a difference in X-ray projection data between respective X-ray tube voltages can be made as large as possible by defining $\Delta t1' < \Delta t2'$ with reference to FIG. 6. FIG. 6 is a schematic diagram showing an example of the X-ray tube voltage property. The second embodiment is effective in a case, for example, that the temporal response property of the X-ray generating section 31 or X-ray detector 34 is slower in switching from the first X-ray tube voltage to the second X-ray tube voltage than in switching from the second X-ray tube voltage to the first X-ray tube voltage. Specifically referring to FIG. 6, as in the first embodiment, in order to make a difference in values of X-ray projection data between respective X-ray tube voltages as large as possible, data collection integration at the first X-ray tube voltage is made when the X-ray tube voltage reaches or exceeds the midpoint M, for example, of the first and second X-ray tube voltages, and data collection integration at the second X-ray tube voltage is made when the X-ray tube voltage decreases down to or below the midpoint M, for example, of the first and second X-ray tube voltages. For the X-ray tube voltage property shown in FIG. 6, a period of time from the timed moment C1 for switching of the X-ray tube voltage to the first X-ray tube voltage to a time at which the X-ray tube voltage reaches the midpoint M of the first and second X-ray tube voltages represents $\Delta t1'$, and a period of time from the timed moment C2 for switching of the X-ray tube voltage to the second X-ray tube voltage to a time at which the X-ray tube voltage reaches the midpoint M of the first and second X-ray tube voltages represents $\Delta t2'$, which is different from $\Delta t1'$. Moreover, $\Delta t1' < \Delta t2'$. Accordingly, data collection is conducted by starting data collection integration at the first X-ray tube voltage after $\Delta t1'$ from the timed moment C1 for switching to the first X-ray tube voltage, and starting data collection integration at the second X-ray tube voltage after $\Delta t2'$ from the timed moment C2 for switching of the X-ray tube voltage to the second X-ray tube voltage, whereby a difference in values of X-ray projection data between respective X-ray tube voltages can be made as large as possible, thus widening a contrast.

Moreover, in the present embodiment, control is made so that the data collection integration time T1' under the first X-ray tube voltage is different from the data collection integration time T2' under the second X-ray tube voltage. As such, however, the number of X-ray photons is different when the X-ray tube voltage and its corresponding magnitude of X-ray tube current are different, resulting in different S/N ratios between the X-ray projection data at the first X-ray tube voltage and that at the second X-ray tube voltage. Accordingly, by defining T1', T2' as described above, a difference in the number of X-ray photons between that under the first X-ray tube voltage and that under the second X-ray tube voltage is adjusted to be equal, and the S/N of the tomographic image at the first X-ray tube voltage (tomographic image from the first X-ray projection data) and that of the tomographic image at the second X-ray tube voltage (tomographic image from the second X-ray projection data) can be made as equal as possible, thus providing a data collection integration time such that image quality of a tomographic image by dual-energy imaging can be improved.

It is generally believed that the number of X-ray photons varies with a change of the X-ray tube voltage in the second or third power. Assuming here that the number of X-ray photons varies with a change of the X-ray tube voltage in the second power, an X-ray tube current value mA1 for the first X-ray tube voltage (140 kV) and an X-ray tube current value mA2 for the second X-ray tube voltage (80 kV), and the data collection integration times T1', T2' are adjusted so that Equation (1) below holds, whereby the number of X-ray photons under the first X-ray tube voltage and that under the second X-ray tube voltage can be made approximately equal to each other:

$$\left(\frac{140(\mathrm{kV})}{80(\mathrm{kV})}\right)^2 \cdot \frac{mA1}{mA2} \cdot \frac{T1'}{T2'} = 1. \quad \text{(EQ. 1)}$$

Moreover, when consecutive tomographic images in the z-direction (direction of the body axis of the subject) in a helical scout scan under the first and second X-ray tube voltages are subjected to weighted addition processing to obtain tomographic images by dual-energy imaging, in order to achieve constant image quality in the tomographic images by dual-energy imaging in the z-direction, the X-ray tube current value for the first and second X-ray tube voltages should be controlled as given below. Here, image noise in the tomographic image at the first X-ray tube voltage and that in the tomographic image at the second X-ray tube voltage is made equal or in a certain constant proportion.

This will be described in more detail hereinbelow. In dual-energy imaging, when applying weighted addition processing to the tomographic images at the first and second X-ray tube voltages, materials or atoms having X-ray absorption coefficients close to those for the material or atoms desired to be extracted or enhanced can be eliminated to conversely highlight the material or atoms desired to be extracted or enhanced. In eliminating such materials or atoms, in order to eliminate those materials or atoms desired to be eliminated, a value of the ratio between the X-ray absorption coefficient under the first X-ray tube voltage and that under the second X-ray tube voltage for the materials or atoms desired to be eliminated can be used to set factors for weighted addition processing on the tomographic images at the first and second X-ray tube voltages to perform weighted addition processing.

For example, representing the absorption coefficient of a certain material under the second X-ray tube voltage as μa, and that under the first X-ray tube voltage as μb, and defining the weighted addition factors wa, wb as given by Equation (2) below, weighted addition processing as given by Equation (3) can be performed to obtain an image with that certain material eliminated. In the equations, a tomographic image at the first X-ray tube voltage of 140 kV is designated as Image140, and that at the second X-ray tube voltage is designated as Image80.

$$\mu a/\mu b = wa/wb, \quad \text{(EQ. 2)}$$

and $$wa \cdot \text{Image80} - wb \cdot \text{Image140}. \quad \text{(EQ. 3)}$$

Thus, when weighted addition processing is performed to obtain a tomographic image with a certain material eliminated, at least one of the factors in the weighted addition processing is negative. When at least one of the weighted addition factors in the weighted addition processing is thus negative, S/N is degraded and image noise is increased as compared with original tomographic images at a plurality of X-ray tube voltages, and a tomographic image by dual-energy imaging provides poorer image quality. Therefore, original X-ray data collection conditions under the plurality of X-ray tube voltages must be determined taking account of exposure to the subject, and in addition, image noise in the tomographic image by dual-energy imaging as well.

Figure 7:
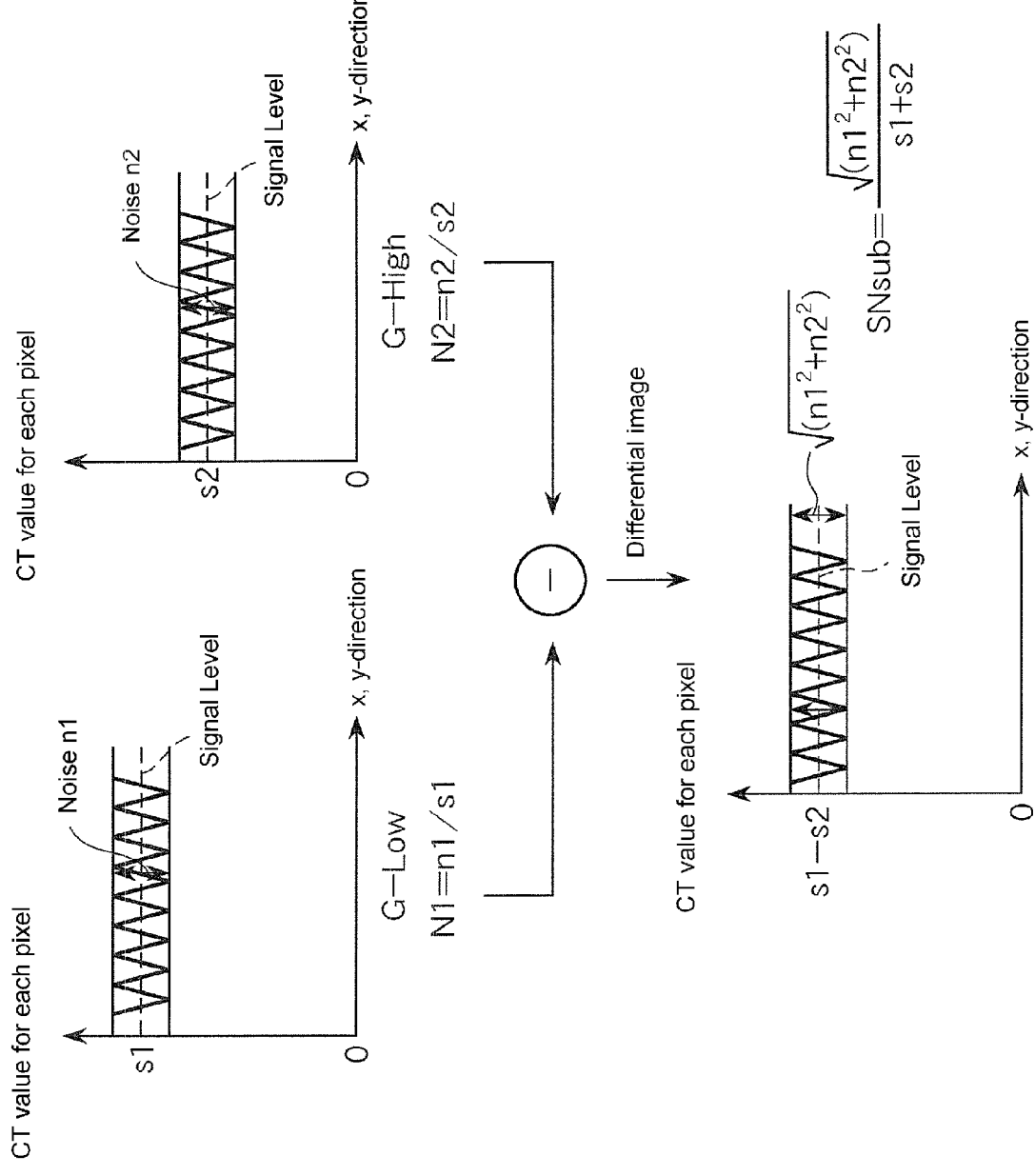
FIG. 7 is a diagram showing image noise in a differential image.

In general, as shown in FIG. 7, a differential image obtained between a tomographic image G-High at a first X-ray tube voltage having image noise of n2, signals of s2, and S/N ratio of n2/s2, and a tomographic image G-Low at a second X-ray tube voltage with image noise of n1, signals of s1, and S/N ratio of n1/s1, has an S/N ratio SNsub as given by Equation (4) below:

$$SNsub = \frac{\sqrt{(n1)^2 + (n2)^2}}{s1 - s2}. \quad \text{(EQ. 4)}$$

Equation (5) given below holds from the theorem of geometric-arithmetic mean:

$$\sqrt{(n1)^2 + (n2)^2} \geq \sqrt{2 \cdot n1 \cdot n2}, \quad \text{(EQ. 5)}$$

wherein the equal sign applies to a condition given by Equation (6):

$$n1 = n2. \quad \text{(EQ 6)}$$

Hence, the following equation Equation (7) holds for the S/N ratio SNsub of the differential image:

$$SNsub \geq \frac{\sqrt{2 \cdot n1 \cdot n2}}{s1 \cdot s2}, \quad \text{(EQ. 7)}$$

wherein the equal sign applies to a condition given by Equation (6).

That is, image noise SNsub in the differential image is minimized when image noise n1 in the tomographic image at the second X-ray tube voltage is equal to image noise n2 in the tomographic image at the first X-ray tube voltage.

Since in the present embodiment, the weighted addition factors are incorporated in weighted addition processing (where a weighted addition factor for the tomographic image at the second X-ray tube voltage is represented as w1, and that for the tomographic image at the first X-ray tube voltage is represented as w2), the foregoing equation can be translated into Equation (8) below taking account thereof:

$$\sqrt{(w1 \cdot n1)^2 + (w2 \cdot n2)^2} \geq \sqrt{2 \cdot w1 \cdot n1 \cdot w2 \cdot n2}, \quad \text{(EQ. 8)}$$

wherein the equal sign applies to conditions given by Equations (9) and (10):

$$w1 \cdot n1 = w2 \cdot n2, \quad \text{(EQ. 9)}$$

and $$n1 = \frac{w2}{w1} \cdot n2. \quad \text{(EQ. 10)}$$

That is, a ratio between image noise n2 in the tomographic image at the first X-ray tube voltage and image noise n1 in the tomographic image at the second X-ray tube voltage can be set to an inverse of the ratio between the weighted addition factor W2 for the tomographic image at the first X-ray tube voltage and the weighted addition factor W1 for the tomographic image at the second X-ray tube voltage.

Moreover, in the present embodiment, the period of time in which the X-ray tube voltage switching signal remains at Low level is twice the period of time in which the X-ray tube voltage switching signal remains at High level. Thus, by making control so that the X-ray emission time is different between the X-ray tube voltages, in addition to controlling the data collection integration time, a difference in the number of X-ray photons can be adjusted to further make the S/N for the X-ray projection data or tomographic image at the first X-ray tube voltage and that for the X-ray projection data or tomographic image at the second X-ray tube voltage as equal as possible, thus providing a data collection integration time such that image quality of a tomographic image by dual-energy imaging can be improved.

According to the second embodiment as described above, a similar effect to that by the first embodiment can be obtained.

Next, a third embodiment will be described. In the following description, only differences thereof from the first and second embodiments will be explained.

Figure 8:
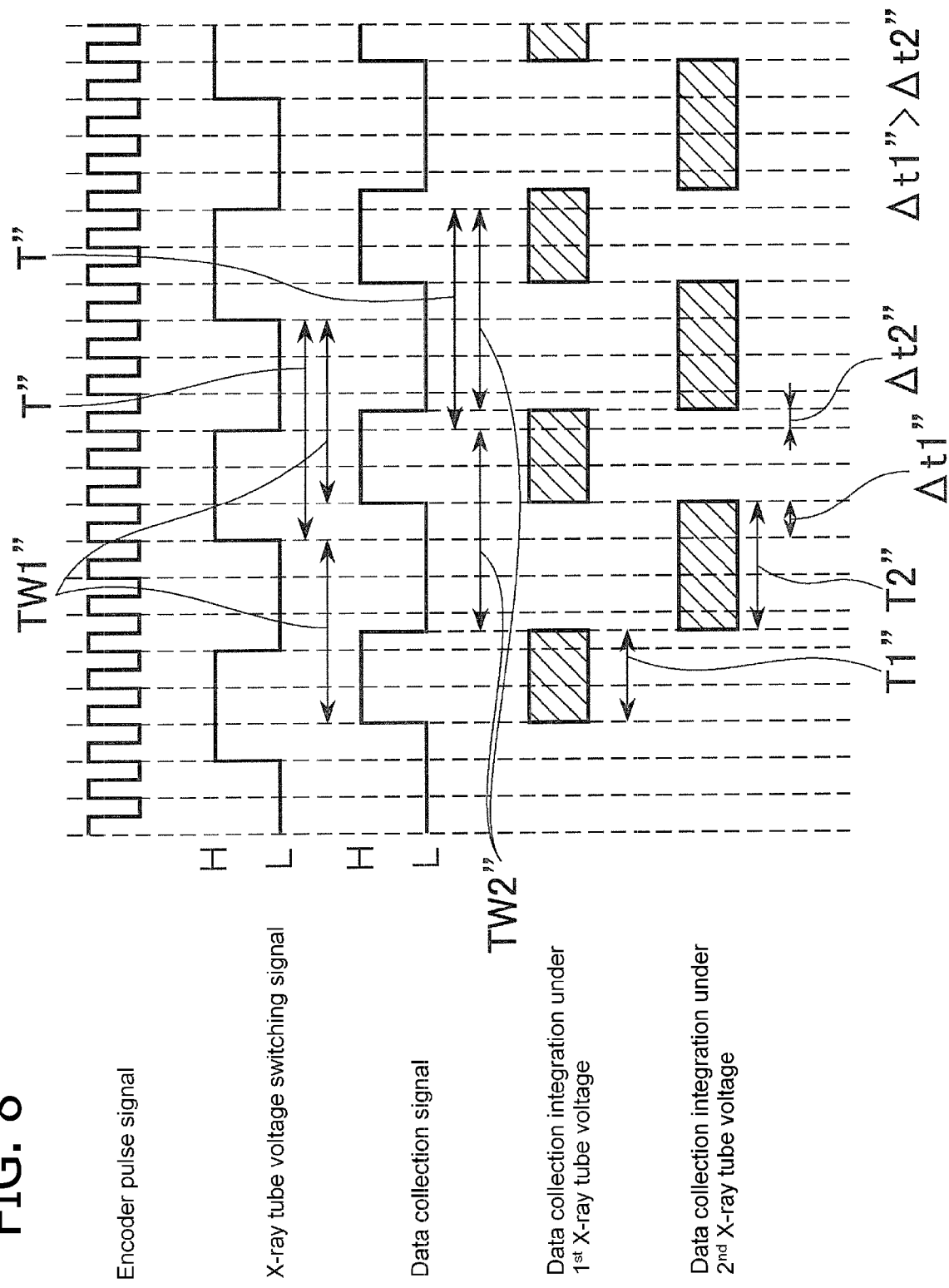
FIG. 8 is a diagram for explaining X-ray projection data collection in the X-ray CT apparatus in a third embodiment.

FIG. 8 is a diagram for explaining X-ray projection data collection in the X-ray CT apparatus in the third embodiment. As shown in FIG. 8, in this embodiment, a period of time $\Delta t1"$ from the timed moment for switching of the X-ray tube voltage to the first X-ray tube voltage to the timed moment for start of data collection integration at the first X-ray tube voltage (i.e., a difference between T" (a cycle of the data collection signal and X-ray tube voltage switching signal) and TW1" (a period of time after the data collection signal has transitioned from Low level to High level until the X-ray tube voltage switching signal transitions from Low level to High level)) has a value different from that of a period of time $\Delta t2"$ from the timed moment for switching of the X-ray tube voltage to the second X-ray tube voltage to the timed moment for start of data collection integration at the second X-ray tube voltage (i.e., a difference between T" and TW2" (a period of time after the data collection signal has transitioned from High level to Low level until the X-ray tube voltage switching signal transitions from High level to Low level)). According to this embodiment, however, $\Delta t1">\Delta t2"$, where $\Delta t1"$ represents a time width twice the pulse width of the encoder pulse signal (or clock pulse signal), and $\Delta t2"$ represents a time width equal to the pulse width of the encoder pulse signal (or clock pulse signal). Accordingly, TW1", TW2", T" are defined to achieve such $\Delta t1"$ and $\Delta t2"$.

Figure 9:
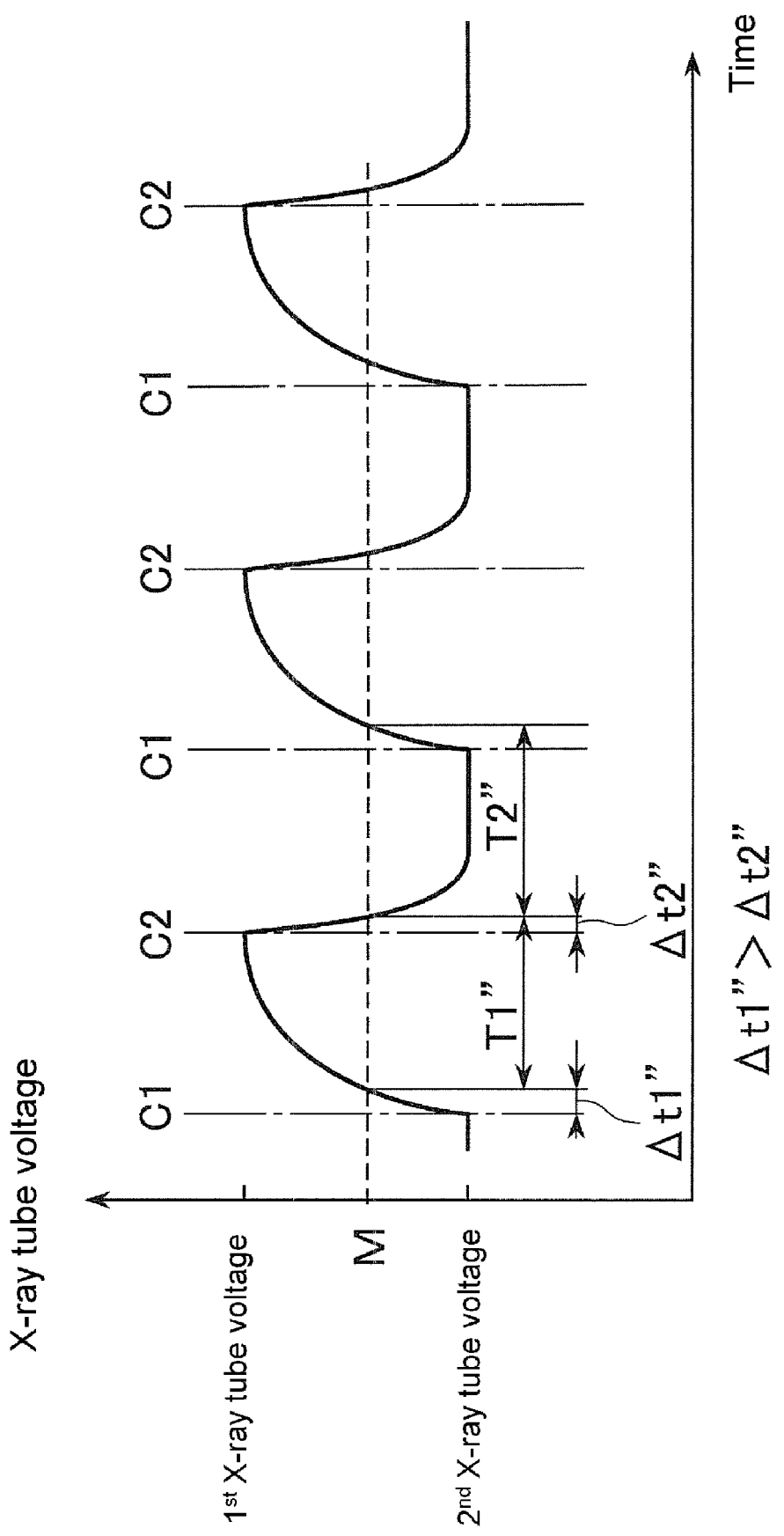
FIG. 9 is a schematic diagram showing an example of the X-ray tube voltage property.

The following description will address X-ray tube voltage property in a case that a difference in X-ray projection data between respective X-ray tube voltages can be made as large as possible by defining $\Delta t1">\Delta t2"$ with reference to FIG. 9. FIG. 9 is a schematic diagram showing an example of the X-ray tube voltage property. As in the first and second embodiments, in order to make a difference in values of X-ray projection data between respective X-ray tube voltages as large as possible, data collection integration at the first X-ray tube voltage is made when the X-ray tube voltage reaches or exceeds the midpoint M, for example, of the first and second X-ray tube voltages, and data collection integration at the second X-ray tube voltage is made when the X-ray tube voltage decreases down to or below the midpoint M, for example, of the first and second X-ray tube voltages. For the X-ray tube voltage property shown in FIG. 9, a period of time from the timed moment C1 for switching of the X-ray tube voltage to the first X-ray tube voltage to a time at which the X-ray tube voltage reaches the midpoint M of the first and second X-ray tube voltages represents $\Delta t1"$, and a period of time from the timed moment C2 for switching of the X-ray tube voltage to the second X-ray tube voltage to a time at which the X-ray tube voltage reaches the midpoint M of the first and second X-ray tube voltages represents $\Delta t2"$, which is different from $\Delta t1"$. Moreover, $\Delta t1">\Delta t2"$. Accordingly, data collection is conducted by starting data collection integration at the first X-ray tube voltage after $\Delta t1"$ from the timed moment C1 for switching to first X-ray tube voltage, and starting data collection integration at the second X-ray tube voltage after $\Delta t2"$ from the timed moment C2 for switching of the X-ray tube voltage to the second X-ray tube voltage, whereby a difference in values of X-ray projection data between respective X-ray tube voltages can be made as large as possible.

Moreover, also in the present embodiment, the data collection integration time T1" under the first X-ray tube voltage is different from the data collection integration time T2" under the second X-ray tube voltage. Thus, by defining such T1", T2", a difference in the number of X-ray photons can be adjusted to make the S/N for the X-ray projection data or tomographic image at the first X-ray tube voltage and that for the X-ray projection data or tomographic image at the second X-ray tube voltage as equal as possible, thus providing a data collection integration time such that image quality of a tomographic image by dual-energy imaging can be improved.

According to the third embodiment as described above, a similar effect to those by the first and second embodiments can be obtained.

While the present invention has been described with reference to the aforementioned embodiments, it will be easily recognized that the present invention is not limited thereto and several modifications may be made without departing from the true spirit of the present invention. For example, while description has been made on helical scanning in the aforementioned embodiments, similar effects can be obtained with conventional scanning (axial scanning), cine scanning, variable-pitch helical scanning, and helical shuttle scanning.

Moreover, while a case in which switching is made between two different X-ray tube voltages is described, the present invention may be similarly applied to a case in which switching is made among a plurality of number, more than two, of X-ray tube voltages.

Furthermore, while description has been made on a case in which no X-ray automatic exposure control mechanism is employed in the X-ray CT apparatus in the aforementioned embodiments, similar effects can be obtained when the X-ray automatic exposure control mechanism is employed in the X-ray CT apparatus.

While a case in which the scan gantry 30 is not tilted is described in the aforementioned embodiments, similar effects can be obtained in so-called tilt scanning in which the scan gantry 30 is tilted.

While description has been made on a case in which X-ray data collection is not synchronous with a biological signal in the aforementioned embodiments, similar effects can be obtained when a biological signal, especially, heart-beat signal, is synchronized.

Moreover, while the aforementioned embodiments address an X-ray CT apparatus with a multi-row X-ray detector, similar effects can be obtained in X-ray CT apparatuses with a two-dimensional X-ray area detector of a matrix structure represented by a flat-panel X-ray detector or with a single-row X-ray detector.

Additionally, in the aforementioned embodiments, helical scanning is achieved by translating the cradle 21 in the z-direction. However, similar effects can be obtained relatively by translating the scan gantry 30 or the rotating section 36 in the scan gantry 30 with respect to the cradle 21.

While the aforementioned embodiments address medical X-ray CT apparatuses, the present invention may be applied to industrial X-ray CT apparatuses, or an X-ray CT-PET apparatus or an X-ray CT-SPECT apparatus in which the X-ray CT apparatus is combined with another apparatus.

The invention claimed is:

1. An X-ray CT apparatus, comprising:
   an X-ray generating section configured to generate X-rays with a plurality of X-ray tube voltages that are switched according to an X-ray tube voltage switching signal;
   a data collecting section configured to synchronously collect, via a data collection signal, X-ray projection data from X-rays with each X-ray tube voltage; and
   a control section configured to control a timed moment for switching the X-ray tube voltage and a timed moment for start of data collection such that the timed moment for start of data collection at each X-ray tube voltage in the data collection signal is delayed relative to the timed moment for switching of the X-ray tube voltage to that X-ray tube voltage in the X-ray tube voltage switching signal by a certain period of time depending upon imaging conditions.

2. The X-ray CT apparatus according to claim 1, wherein said control section is configured to control the delay by a certain period of time based on the X-ray projection data at each X-ray tube voltage.

3. The X-ray CT apparatus according to claim 1, wherein said control section is configured to generate the X-ray tube voltage switching signal with reference to the data collection signal such that the timed moment for start of data collection at each X-ray tube voltage in the data collection signal is delayed relative to the timed moment for switching the X-ray tube voltage to that X-ray tube voltage in the X-ray tube voltage switching signal.

4. The X-ray CT apparatus according to claim 1, wherein said control section is configured to generate the data collection signal with reference to the X-ray tube voltage switching signal such that the timed moment for start of data collection at each X-ray tube voltage in the data collection signal is delayed relative to the timed moment for switching the X-ray tube voltage to that X-ray tube voltage in the X-ray tube voltage switching signal.

5. The X-ray CT apparatus according to claim 1, wherein said control section is configured to set the delay by a certain period of time to be the same for all operations of switching to another X-ray tube voltage.

6. The X-ray CT apparatus according to claim 1, wherein said control section is configured to set the delay by a certain period of time to be different between operations of switching to another X-ray tube voltage.

7. The X-ray CT apparatus according to claim 1, further comprising a setting means configured to set a period of time from the timed moment for switching of the X-ray tube voltage to each X-ray tube voltage to the timed moment for start of data collection at that X-ray tube voltage.

8. The X-ray CT apparatus according to claim 7, wherein said setting means is configured to set the period of time from the timed moment for switching the X-ray tube voltage to each X-ray tube voltage to the timed moment for start of data collection at that X-ray tube voltage such that an enhanced tomographic image image-reconstructed based on the X-ray projection data at respective X-ray tube voltages has a relatively large contrast between different materials.

9. The X-ray CT apparatus according to claim 7, wherein said setting means is configured to set the period of time from the timed moment for switching the X-ray tube voltage to each X-ray tube voltage to the timed moment for start of data collection at that X-ray tube voltage such that tomographic images at respective X-ray tube voltages image-reconstructed from X-ray projection data at said respective X-ray tube voltages have a relatively large ratio of pixel values representing a specific material.

10. The X-ray CT apparatus according to claim 1, wherein said control section is configured to control the timed moment for start of data collection at each X-ray tube voltage based a timed moment for start of data collection integration by said data collecting section.

11. The X-ray CT apparatus according to claim 1, further comprising a pulse signal generating section configured to detect a rotation angle of said X-ray generating section, wherein a period of time from the timed moment for switching the X-ray tube voltage to each X-ray tube voltage to the timed moment for start of data collection at that X-ray tube voltage is one of equivalent to a pulse width of a pulse signal generated by said pulse signal generating section and a multiple of the pulse width of the pulse signal.

12. The X-ray CT apparatus according to claim 1, further comprising a clock pulse generating section, wherein a period of time from the timed moment for switching the X-ray tube voltage to each X-ray tube voltage to the timed moment for start of data collection at that X-ray tube voltage is one of equivalent to a pulse width of a clock pulse signal generated by said clock pulse generating section and a multiple of the pulse width of the clock pulse signal.

13. The X-ray CT apparatus according to claim 1, wherein said control section is configured to provide a different data collection time for each X-ray tube voltage such that X-ray projection data at respective X-ray tube voltages have equivalent noise, or tomographic images at respective X-ray tube voltages image-reconstructed based on the X-ray projection data at the respective X-ray tube voltages have equivalent noise.

14. The X-ray CT apparatus according to claim 13, wherein said control section is configured to provide a period of time from the timed moment for switching the X-ray tube voltage to a next timed moment that is different between respective X-ray tube voltages such that X-ray projection data at respective X-ray tube voltages have equivalent noise, or tomographic images at respective X-ray tube voltages image-reconstructed based on the X-ray projection data at the respective X-ray tube voltages have equivalent noise.

15. An X-ray CT imaging method, comprising:
   generating X-rays with a plurality of X-ray tube voltages that are switched according to an X-ray tube voltage switching signal; and
   synchronously collecting, via a data collection signal, X-ray projection data from X-rays with each X-ray tube voltage, wherein a timed moment for switching the X-ray tube voltage and a timed moment for start of data collection are controlled such that the timed moment for start of data collection at each X-ray tube voltage in the data collection signal is delayed relative to the timed moment for switching the X-ray tube voltage to that X-ray tube voltage in the X-ray tube voltage switching signal by a certain period of time depending upon imaging conditions.

16. The X-ray CT imaging method according to claim 15, further comprising controlling the delay by a certain period of time based on the X-ray projection data at each X-ray tube voltage.

17. The X-ray CT imaging method according to claim 15, further comprising setting a period of time from the timed moment for switching the X-ray tube voltage to each X-ray tube voltage to the timed moment for start of data collection at that X-ray tube voltage.

18. The X-ray CT imaging method according to claim 17, wherein setting a period of time comprises setting the period of time from the timed moment for switching the X-ray tube voltage to each X-ray tube voltage to the timed moment for start of data collection at that X-ray tube voltage such that an enhanced tomographic image image-reconstructed based on the X-ray projection data at respective X-ray tube voltages has a relatively large contrast between different materials.

19. The X-ray CT imaging method according to claim 17, wherein setting a period of time comprises setting the period of time from the timed moment for switching the X-ray tube voltage to each X-ray tube voltage to the timed moment for start of data collection at that X-ray tube voltage is such that tomographic images at respective X-ray tube voltages image-reconstructed from X-ray projection data at each respective X-ray tube voltages have a relatively large ratio of pixel values representing a specific material.

20. The X-ray CT imaging method according to claim 15, further comprising setting the timed moment for start of data collection at each X-ray tube voltage as a timed moment for start of data collection integration.

* * * * *